United States Patent [19]
Oeschger et al.

[11] 4,337,314
[45] Jun. 29, 1982

[54] GENETICALLY ATTENUATED BACTERIAL VACCINES WITH MULTIPLE MUTATIONS OF THE SAME PHENOTYPE

[75] Inventors: Max P. Oeschger, Silver Spring, Md.; Anne M. Hooke, Annandale, Va.; Joseph A. Bellanti, Bethesda, Md.

[73] Assignee: Research Corporation, New York, N.Y.

[21] Appl. No.: 41,896

[22] Filed: May 23, 1979

[51] Int. Cl.$^3$ .............................................. C12N 1/20
[52] U.S. Cl. .................................. 435/253; 435/172; 435/851; 424/92
[58] Field of Search ................... 435/172, 253, 851; 424/92

[56] References Cited

U.S. PATENT DOCUMENTS

| | | | |
|---|---|---|---|
| 3,855,408 | 12/1974 | Maheswaran | 424/92 |
| 3,856,935 | 12/1972 | Geornanier | 424/92 |
| 3,992,522 | 11/1976 | Chanoch et al. | 424/89 |
| 4,133,875 | 1/1979 | Hilhman | 424/93 |
| 4,190,495 | 2/1980 | Curtiss | 435/172 |

FOREIGN PATENT DOCUMENTS 1516458  7/1978  United Kingdom .

OTHER PUBLICATIONS

Spring et al., Virology 66, 522–532 (1977).
Murphy et al., Journal of Infectious Diseases 134, 577 (1976).
Murphy et al., International Symposium on Influenza Immunization (II), 39, 47(1977).
Murphy et al., Journal of Infectious Diseases 130, 144, (1974).
Research Resources Reporter, Dec. 1978, vol. II, No. 12.
Curtiss III, Annual Reviews of Microbiology, 1976 30:507–33.
Lamanna et al., Basic Bacteriology 3rd Ed., The Williams & Wilkins Co., pp. 723–727 (1965).
Metzler, Biochemistry, The Chemical Reactions of Living Cells, Academic Press, Inc., pp. 945 & 946 (1977).

Primary Examiner—Alvin E. Tanenholtz
Attorney, Agent, or Firm—Oblon, Fisher, Spivak, McClelland & Maier

[57] ABSTRACT

A vaccine composition comprising a genetically attenuated bacterial strain which contains at least two mutations of the same phenotype which strain is rendered avirulent while retaining immunogenicity.

7 Claims, 5 Drawing Figures

GENETICALLY ATTENUATED BACTERIAL VACCINES WITH MULTIPLE MUTATIONS OF THE SAME PHENOTYPE

BACKGROUND OF THE INVENTION

1. Field of the Invention

This invention relates to bacterial vaccines comprising genetically-attenuated strains and to processes for their preparation.

2. Description of the Prior Art

The use of bacterial and viral vaccines has been very successful in the prevention of infectious diseases in humans and other animals. There are various methods of preparing vaccines from viruses or bacteria. The basic requirements for any vaccine and for a method for the preparation of a vaccine are that (1) the resulting vaccine contain the necessary antigenic determinants to induce formation of antibodies in the host; (2) the vaccine possess high immunogenic potential; (3) the resulting vaccine be safe enough to be administered without any danger of clinical infection, either for the recipient or any contact of the recipient, and, therefore, the risk associated with vaccination be minimized, if not totally eliminated; (4) the resulting vaccine be devoid of any toxic side-effects, for example, fever from endotoxin present in killed or extracted cells; (5) the resulting vaccine be suitable for administration by an effective route, for example, oral, intranasal, topical or parenteral; (6) the resulting vaccine and its mode of administration mimic closely the circumstances of natural infection; (7) the resulting vaccine be stable under conditions of long-term storage, and that said long-term storage be at room temperature and (8) the resulting vaccine be compatible with the usual inert vaccine carriers.

Prior art methods which have attempted to fulfill one or more of the aforementioned requirements include vaccines containing killed whole cells, purified or partially-purified selected antigenic components, and live, chemically- or genetically-attenuated microorganisms.

The use of killed whole cells as vaccines has been described by Switzer et al., in U.S. Pat. No. 4,016,253, who applied such a method to the preparation of a vaccine against *Bordetella bronchiseptica* infection in swine. Killed whole cells have also been used to prepare a vaccine against chronic bronchitis caused by *Haemophilus influenzae* (Brown and Wilson, Br. Med. J. 1:263, 1959). The use of killed cells, however, is usually accompanied by an attendant loss of immunogenic potential, since the process of killing usually destroys or alters many of the surface antigenic determinants necessary for induction of specific antibodies in the host. The antibodies produced in response to such altered antigens are not as specific for the molecular structures on the surface of the live organism, and, therefore, are not as effective against the invading pathogen.

Antigenic components, isolated and purified from microorganisms, have also been used as vaccines. This is represented, for example, by the use of purified capsular polysaccharide material of *H. influenzae* type b as a vaccine against the meningitis caused by this organism in humans (Parke et al., J. Inf. Dis. 136(Suppl.):S51, 1977; Anderson et al., J. Inf. Dis. 136(Suppl.):S63, 1977; Mäkela et al., J. Inf. Dis. 136(Suppl.):S43, 1977). This approach, however, also suffers from drawbacks, in that it requires isolation and purification techniques which may seriously compromise the detailed three dimensional spatial arrangement of the antigen upon freeing it from its position in the whole cell. The inherent immunogenicity of the antigens extracted from whole cells may also be diminished—a loss which may contribute to the relative lack of success with such vaccines in very young children (references supra; Davies, J. Immunol. 33:1, 1937 and Monto et al., J. Inf. Dis. 127:394, 1973). Thus, immunization of older children and adults with purified capsular polysaccharide from *H. influenzae* type b does induce humoral antibody, while the very young (less than 14–18 months) who are most susceptible to the disease fail to mount a significant, lasting response (references, supra). Similar difficulties have been encountered when purified capsular polysaccharide vaccines are prepared from *Streptococcus pneumoniae* and *Neisseria meningitidis* and used to immunize young children (Davies, J. Immunol. 33:1, 1937; Monto, et al., J. Inf. Dis. 127:394, 1973).

Chemically-attenuated, live microorganisms have also been used as vaccines in the prior art. This method of preparing vaccines is represented, for example, by the work of Wilson in U.S. Pat. Nos. 3,907,987 and 3,975,517. Wilson prepared a live, bacterial vaccine against coliform enteritis in animals from selected strains of *Escherichia coli* which were treated with dilute formalin in order to render them less virulent. Bauer et al., U.S. Pat. No. 4,058,599 describes the preparation of inactive but immunogenic microorganisms, which were treated with ethyleneimine and therefore rendered less infectious. The chemical treatment of whole microorganisms may severely impair their immunogenic potential, and in many cases may not decrease virulence as much as desired.

A second technique for attenuating the virulence of live microorganisms while allowing them to retain immunogenic potential, is the development of avirulent or slow-growing strains, or mutants incapable of sustained replication in the host. Such mutants, if well chosen, will maintain the full integrity of cell-surface constituents necessary for specific antibody induction, yet will be unable to cause disease, because they (1) fail to produce virulence factors, (2) grow too slowly, or (3) grow not at all in the host. A variety of such genetic variants have been used to prepare bacterial and viral vaccines.

Smith (U.S. Pat. No. 3,364,117), Hillman (U.S. Pat. No. 4,133,875) and Germanier (U.S. Pat. No. 3,856,935) have all described vaccine strains which have lost the ability to cause disease presumably because of mutations in genes responsible for the production of virulence factors. The vaccine described by Smith (supra) comprised a "rough" variant of *Salmonella cholerasuis* which was poorly characterized, except for its loss of virulence in pigs. Since the mutant is rough, the surface properties are altered, and, therefore, not truly representative of the antigens of the pathogenic form. Hillman (supra) described a well-characterized mutant strain of *Streptococcus mutans* which has a single point mutation in the structural gene that codes for the enzyme L(+)-lactate dehydrogenase. This mutant strain is a low-acid producer and potentially can replace the normal high-acid producing *Streptococcus mutans* in oral flora in order to reduce the incidence and severity of dental caries in humans. Germanier (supra) described a mutant strain of *Salmonella typhi* carrying a single mutation (characterized as a deletion) which profoundly affects the expression of the genes encoding the galactose-metabolising enzymes. These genes are clustered in a unit, the gal operon, which encodes the information for the synthesis of three enzymes—uridine diphosphogalactose-4-epimerase, galactose-1-phosphate uridylyltransferase and galactokinase. The deletion in this strain has occurred in the epimerase gene which prevents the production of any functional epimerase enzyme. Characteristically such a deletion also exerts strong polar effects on the distal genes of the operon (Martin et al., Cold Spring Harbor Symp. Quant. Biol. 31:215, 1966) hence the levels of galactokinase and galactose-1-phosphate uridylyl-transferase are markedly reduced in this strain. Deletions are usually stable and no revertants of this strain have been detected. However, such galE mutations cause alterations in surface properties by preventing the complete formation of the lipopolysaccharide side chains. Hence, the very structures responsible for inducing type-specific antibodies are compromised. In addition, galE mutations can result in autolysis, thereby compromising the ability of the vaccine strain to produce prolonged immunological stimulation.

Influenza and respiratory syncytial virus mutant strains which replicate slowly at human body temperature (37° C.) and thus are unable to cause disease, have been prepared (Murphy et al., J. Inf. Dis. 128:479, 1973 and Chanock et al., Pediatr. Res. 11:264, 1977). These single mutation strains have proven to produce so many virulent revertants in the vaccinee that they are not practical. There are no reports of slow-growing bacterial mutant strains appropriate for use as vaccines, but the same limitations which apply to the slow-growing viral strains would also apply to them.

Two classes of mutants have been used to prepare vaccine strains which do not replicate at all in the host. The first class includes strains which are dependent upon unusual nutrients or growth factors (compounds outside the biochemistry of the vaccinee) for replication as described by Levine (J. Inf. Dis. 133:424, 1976) and Reitman (J. Inf. Dis. 117:101, 1967). These workers described strains of *Salmonella typhi* and *Salmonella typhosa* which require streptomycin for growth. Presumably the structure of ribosomal proteins in these strains is modified so that streptomycin is required for proper ribosome function. These strains, however, do not have sufficient genetic stability to make them truly safe vaccines.

The second class includes strains which are incapable of replication above certain temperatures as described by Fahey and Cooper (Infect. Immun. 1:263, 1970), Maheswaran (U.S. Pat. No. 3,855,408) and Helms et al., (J. Inf. Dis. 135:582, 1977). Temperature-sensitive strains of *Salmonella enteritidis, Pasteurella multocida* and *Streptococcus pneumoniae* were isolated and partially-characterized by these workers. The strains were unable to grow at the body-temperature of the animals they were tested in, but were excellent immunogens, since the surface properties of the cells were unaltered. Significant reversion to virulence, however, has precluded their use in humans and other animals.

The reversion problem associated with attempts to use temperature-sensitive strains as vaccines appears to be an inherent limitation of the approach. This is because ts mutations result from single base changes and therefore exhibit significant spontaneous reversion. Similarly, reversion (to virulence) has also posed a problem in the safety of employing genetically-attenuated viral strains as vaccines (Henderson et al., J.A.M.A. 190:41, 1964; Chanock et al., Pediatr. Res. 11:264, 1977 and Murphy et al., J. Inf. Dis. 128:479, 1973)

In order to overcome this problem, the prior art has investigated the vaccine potential of virus strains which contain two growth-attenuating mutations (Murphy et al., Virology 88:231, 1978 and Murphy et al., Infect. Immun. 23:249, 1979). In such strains, two mutations of different phenotype were combined with the expectation that the reversion frequencies would decrease.

Two methods have been used to combine multiple ts mutations in one strain. First, Chanock et al., (Pediatr. Res. 11:264, 1977) mutagenized a strain of respiratory syncytial virus which already contained a ts mutation, and isolated a strain which contained a second ts lesion. The first mutation almost completely blocked virus replication at 39° C.; the second mutation severely limited replication at 37° C., and so the double mutant strain could be recognized.

A second method using natural in vivo recombination was reported by Murphy et al., (Virology 88:231, 1978). They constructed a doubly ts strain of influenza virus by co-infecting cells with two virus strains, one containing a mutation with a cut-off temperature of 37° C. and the second containing a mutation in another gene with a cut-off temperature of 38° C., and isolating recombinant viruses among the progeny. The rationale for preparation of these strains was that the resulting isolates would contain two growth restricting mutations, the original mutation which severely restricts replication at 38° or 39° C. and a second mutation which severely restricts replication at or above 37° C. At temperatures of 39° C. or above both mutations severely limit virus replication; and revertants are extremely rare (as outlined above). However, at 37° C., normal human body temperature, only one of the two mutations will limit growth and the virus will phenotypically express only one mutation; resulting in a reversion frequency equal to that of the 37° C. mutation alone. Double-ts mutant strains, where the temperature cut-off points are not the same, can also produce significant numbers of revertants of one of the ts mutations if they are propagated at temperatures near the lower cut-off temperature. Such temperatures are semi-permissive and provide strong selective pressure for overgrowth of the original strain by revertants.

While the use of multiple mutations has not been applied to bacterial vaccine strain preparation, Curtiss has constructed a strain of *Escherichia coli* which is attenuated by the incorporation of multiple mutations of different phenotype, for gene cloning (Ann. Rev. Microbiol. 30:507, 1976). The important consideration in this work was to produce a strain that could not survive outside a specialized environment provided in the laboratory. In fact, at least one of the mutations introduced into the strain causes the self-destruction of the cell when it attempts to grow outside the defined specialized environment. Curtiss has suggested that this strain could be used to clone the gene(s) for a bacterial toxin which could then be produced in bulk for vaccine use (ibid, at 510, lines 26–28). Furthermore, British patent specification No. 1-516-458, published by July 5, 1978 in the United Kingdom, describes this microorganism, *Escherichia coli* K-$12_{\chi}$1776 and the many mutations which have been introduced into it in order to make it safe for the large-scale production of prokaryotic or eukaryotic proteins (for example, cholera toxin or insulin), or organic acids (for example, succinic or lactic acid produced by fermentation of glucose). The specification describes on p.4 the use of microorganisms which have been precluded from growth or colonization in natural ecological niches. However, the main thrust of the specification is directed towards the construction of bacterial strains containing various mutations conveying many different phenotypes in one strain. The disadvantage of using such an approach for construction of vaccine strains are discussed below.

The combination of two mutations of different phenotype in a single strain will only be effective in reducing the revertant frequency when both mutations are simultaneously restrictive. This argument is equally applicable to temperature-sensitive, growth factor or virulence factor mutations, alone or in combination. Ideally, to achieve reduced reversion frequencies by combining two or more mutations in a single strain, the mutations must convey identical phenotypes so as to ensure that they always work in concert.

SUMMARY OF THE INVENTION

It is therefore an object of the invention to provide a safe vaccine based on live, genetically-attenuated bacterial microorganisms. It is another object of the invention to provide vaccines based on bacterial strains carrying two or more mutations.

It is a further object of the invention to provide bacterial vaccines based on strains which contain two or more mutations of the *same* phenotype.

Still another object of the invention is to provide bacterial vaccines based on strains which contain two or more temperature-sensitive mutations which have an identical cut-off or restrictive temperature.

Still a further object of the invention is to provide bacterial vaccines based on strains which maintain antigenic integrity and remain intact after administration.

An object of the invention is to provide bacterial vaccines based on strains which are capable of at least limited replication in the host, in order to simulate the initiation of normal infection.

Still a further object of the invention is to provide a bacterial strain which is suitable as a vaccine for *Haemophilus influenzae* per se, and, by genetic addition of appropriate capsular information, vaccines for any and all serotypes of *Haemophilus influenzae*.

An object of the invention is also to provide a method of inoculation against infectious diseases by using genetically-attenuated bacterial vaccine strains which contain two or more mutations of the same phenotype.

Another object of the invention is also to provide a process for the preparation of genetically-attenuated vaccine strains containing two or more mutations of the same phenotype.

These and other objects of the invention as hereinafter will become more readily apparent have been attained by providing a vaccine comprising a genetically-attenuated bacterial strain which contains two or more mutations of the same phenotype which strain is rendered avirulent while retaining immunogenicity.

The objects of the invention have also been attained by providing a vaccine wherein the two or more mutations of the same phenotype are temperature-sensitivity mutations of the same phenotype.

The objects of the invention have also been attained by providing a vaccine against meningitis and other diseases caused by the organism, which comprises a genetically-attenuated strain of *Haemophilus influenzae* which contains at least two different ts mutations of the same phenotype.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein FIG. 1 describes the protocol used for isolating ts mutants of *H. influenzae*.

DETAILED DESCRIPTION OF THE PREFERRED EMBODIMENTS

The essential properties of vaccines are that they: (1) effectively induce protective immunity in the vaccinee, (2) do not produce disease and (3) do not have toxic side-effects. Other desirable properties of vaccines include: (1) inability to establish carrier-states for communicable pathogens, (2) inexpensive and simple preparation, (3) stability and (4) ease of administration. The vaccine preparations described in this invention meet all these requirements, for they: (1) use whole cells whose surface antigens are identical with those of the pathogen against which immunity is sought; hence they possess high immunogenic potential, making low doses effective and minimizing dose-dependent toxic side-effects, (2) use genetically-attenuated, live cells which cannot cause disease in the vaccinee, (3) are essentially free of virulent forms of the pathogen (less than one virulent cell per sextillion [$10^{21}$] vaccine organisms) and (4) can be cultured, stored and administered by standard microbiological and immunological procedures.

Specifically, this invention describes a method for the preparation of safe, effective, live vaccine strains. This has been accomplished by combining multiple attenuating mutations of identical phenotype into otherwise normal pathogenic strains, thus rendering the strain avirulent in the normal host.

ADVANTAGES OF LIVE, GENETICALLY-ATTENUATED VACCINES

One advantage of working with live, mutant microorganisms, as opposed to isolated antigenic components, is that it ensures, at least for mutations which do not affect cell-surface and extracellular antigenic components, the presence of all essential structural features necessary for succesful induction of antibody synthesis in the host. It is well established that the detailed three-dimensional arrangement of the antigen-combining site is highly specific and necessary for molecular recognition of antigen by antibody. (Kabat, Structural Concepts in Immunology and Immunochemistry, Holt, Rinehart and Winston, Inc., 1968; chapter 6). If the three dimensional molecular arrangement of the antibody-inducing vaccine is not as close as possible to the molecular arrangement of the antigens of the infecting microorganism, then the antibodies formed against the inducing vaccine will not be very successful against the challenger. In other words, the avidity of these antibodies for the "natural" antigens will be low. If the vaccine is antigenically identical with the microorganism which will pose the eventual challenge, the avidity of the antibodies formed against the vaccine, and therefore, also against the antigens of the pathogen is correspondingly very high.

The vaccines of the present invention also embody the specific advantage of maintaining the inherent adjuventicity of whole cells. The potentiation of the immunogenicity of certain antigens (for example, polysaccharides) by other cellular components is well-documented. The present invention exploits this property maximally.

A further specific advantage of the present invention is that vaccines prepared from strains with the appropriate attenuating mutations, can grow in the recipient and mimic natural infection.

SPECIFIC FEATURES OF THE INVENTION

The most important element of this invention is that the microorganisms have multiple mutations of the same phenotype in the same strain. This feature creates a protective guard against reversion of the mutated strain to the virulent form. It also provides a solution to a long recognized need in the art of genetically-attenuating bacterial vaccines. The genetic instability of viral and bacterial mutants has long been one of the most serious obstacles to the widespread use of genetically-attenuated strains as vaccines. The present invention has accomplished a breakthrough in this respect and opens the door to the extensive use of mutant strains as vaccines. It overcomes the problem of reversion in mutated strains by reducing the effective reversion frequency of such strains to negligible levels ($<10^{-20}$). This has been accomplished by incorporating multiple, independent mutations which convey the same phenotype, into a single strain. The two or more independent mutations used render the strain incapable of causing disease in the host. The reversion rate of a strain containing multiple mutations of the same phenotype is the product of the reversion frequencies of the individual mutations. If three mutations, each with a reversion frequency of ca. $10^{-7}$, are combined, a strain with a reversion rate of $10^{-21}$ is obtained. This means that if every man, woman and child presently on earth and all future generations were immunized with such a vaccine, using a dose of one million organisms per vaccinee, only one individual in the next ten million years ($10^{15}$ people) would be exposed to a virulent revertant!

CHOICE OF ATTENUATING MUTATIONS

An important aspect of the solution to the reversion problem presented in this invention, is that all the mutations affect functions which cannot be corrected under the normal physiological conditions of the host. Potentially, such mutants include (1) those that do not produce virulence factors in the host, (2) those dependent upon the presence of growth factors not normally found in the host and (3) those unable to sustain replication at the body temperature of the host.

The first group, those which do not produce virulence factors in the host, can be defined as mutants unable to make functional virulence factor(s) under any conditions or under the physiological conditions of the host. Such mutants, for example, may only produce non-toxic, but immunogenic fragments of a toxin, may produce no toxin at the body temperature of the host, or may be incapable of producing toxin under any condition. Such mutants would also include strains unable to produce factors necessary for tissue invasion. Such mutants would also include strains unable to make pili required for adherence to animal cells (colonization factors), although it should be recognized that such vaccine strains may thereby suffer loss of important antigens and the ability to persist in the area necessary to alert the immune system.

The second group can be divided into two classes. First, those mutants unable to synthesize intermediate metabolites unique to procaryotic organisms. One example is diaminopimelic acid (DAP), a compound not found in the biochemistry of eukaryotic organisms, but which is an essential intermediate in the biosynthesis of cell-wall material in many bacterial species. In the absence of DAP such strains lyse as a result of cell growth. Second, those mutants that require certain compounds which are not metabolized but are essential for growth. Mutant strains which require streptomycin fall into this class.

The third group, temperature-sensitive (ts) mutants, contain lesions which do not permit sustained replication of the organism at the body temperature of the host. When these lesions directly affect essential functions, such as transcription, translation or transport, they cannot be corrected by any environmental factor other than temperature. Hence, temperature-sensitive mutations which affect essential functions have a distinct advantage over growth-factor dependent mutations for there is always the chance that unique microbial metabolites could be supplied by host flora or iatrogenic intervention.

Specifically, temperature-sensitive mutations can be divided into four classes: (1) those that cause growth to terminate "immediately" on transfer to the non-permissive temperature; (2) those that restrict the growth rate at the non-permissive temperature; (3) those that grow and lyse, and (4) those that have little or no immediate effect on growth, but terminate growth following a number of cell-divisions at the restrictive temperature. The first class allows precise control over the number of organisms used to inoculate the individual vaccinee, but since growth is "immediately" terminated following inoculation, the immunogenic potential of the vaccine may be compromised because early steps in the disease process cannot be mimicked. The second class of ts mutations, those which allow slow growth at the restrictive temperature, can provide long-term exposure to the microbial antigens but, since such strains can replicate ad infinitum at the restrictive temperature, there is no way to eliminate the possibility that the vaccinee will be exposed to virulent revertants. The third class of ts mutations, those which bring about lysis at the restrictive temperature, may cause removal of the vaccine organisms before the immune system has a chance to respond to their presence. The fourth class of ts mutations, those which initially allow "normal" replication after transfer to the restrictive temperature, but completely block sustained replication in the vaccinee, can be used to produce vaccine strains which can, upon inoculation, initiate normal infective processes, but which cannot cause disease.

The most essential feature of the approach herein presented is that all the mutations in a given strain convey the same phenotype. This feature is important in that it ensures that all of the mutations incorporated work in concert. Hence, the effective reversion frequency is guaranteed always to be the product of the reversion frequencies of the individual lesions. To further elaborate this point the bacterial vaccines of the present invention carry multiple (i.e., two or more) mutations, with each independent mutation conveying the same phenotype. Thus, in one embodiment of this invention a bacterium may, for example, carry two 37° C. ts lesions, $ts_1$ and $ts_2$. The resulting microorganism is unable to grow at 37° C. or higher temperatures. Without being bound by any particular theory, Applicants suggest that such a bacterium probably has two different mutations which affect two different proteins essential for growth, $protein_1$ and $protein_2$. In the multiple mutant strain neither protein is functional at 37° C. or higher temperatures, but both proteins are functional at lower temperatures. If the $ts_1$ mutation should spontaneously revert, the $protein_1$ produced will be functional at 37° C. Since $ts_2$ has not reverted, however, $protein_2$ remains non-functional at 37° C. and hence the growth and replication of the revertant is still restricted at 37° C. Not until $ts_1$ and $ts_2$ have both reverted will the cell produce functional $protein_1$ and $protein_2$, and regain the capacity to grow at 37° C. The same model may be applied to other mutations, such as antibiotic-dependent mutations or the like. The fulfilment of this requirement (identical phenotypes) may be practically difficult, for example, with multiple streptomycin-dependent mutations when all the lesions would have to reside in the same gene. Not only would such a strain be technically difficult to construct, but also, in the event of in vivo genetic exchange, incorporation of one small piece of DNA could eliminate all the lesions. There is no such restriction on temperature-sensitive mutations, for multiple lesions can be widely distributed in the genetic material. Hence, the probability for correction of the lesions is reduced by the product of the probabilities for in vivo genetic correction of each individual lesion. The probability of this happening (in vivo genetic recombination) with widely separated mutations is so low as to not to constitute a problem (Curtiss, Ann. Rev. Microbiol. 30:507, 1976).

ISOLATION OF MUTANT STRAINS

Strains containing attenuating mutations can originate either as spontaneous derivatives or after mutagenic treatment. Not only can mutagenic treatment be applied to whole organisms but also to DNA which contains relevant genetic information (provided that the DNA is subsequently incorporated into the whole organism). When the mutation confers a selectable phenotype, the mutant derivatives can be isolated and identified by standard genetic techniques. Mutations which confer a phenotype only detectable by specialized techniques can be identified by employing those techniques (for example, see Maas et al., Proc. Nat. Acad. Sci. 75:1384, 1978). Detailed descriptions for the isolation of mutant strains whose replication is temperature-sensitive are presented in the next section.

CONSTRUCTION OF MULTIPLE MUTANT STRAINS

An important feature of this invention is that the multiple mutations which are combined into a vaccine strain convey the same phenotype. The fact that each mutation exhibits an identical phenotype precludes direct selection of multiple mutant strains, for there is no simple way to distinguish between single and multiple mutant isolates. We have solved this problem by isolating individual mutant strains containing single attenuating mutations, and then transferring these mutations into a single strain (by genetic transfer and recombination). To facilitate the detection of strains which have incorporated the desired attenuating mutation(s) each attenuating mutation used is genetically linked to a readily selectable and scorable "non-attenuating" allele. The linked markers are selected in the strain constructions and then the simultaneous incorporation of the desired attenuating mutation(s) tested among the recombinants.

Two classes of phenotype lend themselves to exploitation for such strain construction: (1) auxotrophy—a strict requirement for an amino acid or nutritional factor, and (2) chromosomal resistance—mutations which convey resistance to selected agents (e.g. antibiotics, colicins, or bacteriophage).

Mutants representing both the above phenotypes can be isolated in a straightforward manner and used for positive genetic selection (e.g. prototrophy—the requirement for a nutritional factor is "cured", or resistance—the ability to grow in the presence of a bactericidal agent). Attenuated mutants are isolated from auxotrophic or wild-type strains. Appropriate selectable markers are introduced as part of the mapping procedure. Strains which attenuating mutations linked to selectable markers are used for the subsequent constructions. Recombinants which have potentially incorporated the attenuating mutations are first identified by selection of the linked selectable marker. Successful concomitant transfer of the attenuating mutation is confirmed by recovery of the mutation from the recombinant (see the following section for a detailed description of such procedures).

MECHANISMS FOR GENETIC TRANSFER AND RECOMBINATION

There are four recognized mechanisms for transfer of genes (DNA) from one bacterial cell to another which may be used to prepare the vaccines of this invention: (1) transformation naked DNA from cell "A" is taken up by cell "B" and incorporated into the chromosome of cell "B" (Alexander the Leidy, J. Ex. Med. 97:17, 1953); (2) transduction—virus particles containing DNA from cell "A" attach to cell "B" and "inject" the DNA into cell "B", where it is incorporated into the chromosome of cell "B" (Lennox, Virology 1:190, 1955; (3) conjugation—cell "A" and cell "B" come together and DNA from cell "A" passes unidirectionally from cell "A" into cell "B" and is incorporated into the chromosome of cell "B" (Wollman et al., Cold Spring Harbor Symp. Quant. Biol. 21:113, 1964) and (4) fusion—cells "A" and "B" are chemically treated, fusion of the two cells occurs and DNA from "A" and "B" transiently reside in the same cell before recombination occurs (Fodor and Alfödi, Proc. Natl. Acad. Sci. 73:2147, 1976). In vitro recombination of genetic information can be accomplished by isolation of DNAs, enzymatic cleavage and insertion of "A" into "B", and then transformation of cells with the hybrid DNA. Any or all of these mechanisms may be used to move genes among bacteria.

Other methods to prepare the bacterial vaccines of the present invention are in vitro mutagenesis of specific DNA molecules (Bautz-Freese and Freese, Virology 13:19, 1961), de novo gene synthesis (Khorana, Science 203:614, 1979) and construction of mutated genes by recombinant DNA technology. Although such methods are in their infancy, it is possible to foresee the selective and specific preparation of a gene with two or more well-defined base changes at the DNA level. Such a well-characterized gene can then be reintroduced into the bacterial chromosome and thus result in the creation of a well-defined mutant. If the two or more base changes are chosen so as to produce two or more different mutations of the same phenotype, then the resulting bacterium will be encompassed by those of the present invention.

ADVANTAGES OF THE MASTER STRAIN

One of the major advantages of the present invention is that the techniques can be applied to introduce multiple mutations of the same phenotype into a "rough" strain of, for example, *Streptococcus pneumoniae,* and then the capsular genes for each clinically-significant serotype (and there are at least 14) can be transformed into the "master" strain to produce a vaccine strain for each. In fact, the multiple-mutant strain of the present invention is a "rough" variant of *H. influenzae,* and it is anticipated that this strain can not only be used as a vaccine to protect from infection with such "untypable" *H. influenzae* (for example, most cases of otitis media in young children are caused by "rough" *H. influenzae*) but it can also be modified by transformation with the capsular genes for the b serotype, making it suitable as a vaccine to protect from influenzal meningitis.

STORAGE

One of the advantages of the present invention is that the vaccine can be easily prepared, lyophilized in the presence of appropriate inert, non-toxic carrier(s) (infra) in vials and stored at room temperature without loss of potency. No refrigeration or special storage equipment is required.

QUALITY CONTROL

The composition of vaccine preparations must be known and consistent. This is achieved by using specified amounts of quality-controlled chemical and biological ingredients in their preparation. Methods for the quality control of chemical components are well established in the art and will not be discussed here. Chemical purity in the vaccine preparations is defined as freedom from toxic waste or cellular breakdown products and interfering or spurious immunogenic material. This is assured by working with pure cultures (the vaccine strain free of other cells or virus) and harvesting the cells while the culture is in the logarithmic phase of growth (before the synthesis of autolytic enzymes). The collection and washing of cells from the medium by physical methods (centrifugation) should leave low molecular weight impurities in the supernatent.

The present invention has certain advantages with respect to quality control of the biological components of the vaccine. Standard techniques can be used to monitor the general biological purity of preparations (freedom from contaminating virus or bacteria). The specific advantages of this invention relates to the second level of biological purity which must be maintained—genetic purity. The most important factor for maintenance of genetic purity in the propagation of genetically-attenuated vaccine strains is the choice of attenuating mutations. It is essential that such mutations do not limit the rate or extent of growth of the strains under all conditions used for maintenance, pilot, or large-scale production. This ensures that when revertants do arise they will not possess any selective growth advantage over the vaccine strain, and hence will not outgrow (and in so doing replace) the vaccine strain in any phase of their culture under permissive conditions. The appearance of revertants can be monitored by plating a portion of culture under non-permissive conditions. The maintenance of the attenuating mutations incorporated in the vaccine strain can be checked by rescue of those mutations from a sample of cells taken from a vaccine preparation.

ADMINISTRATION

The vaccines of the present invention can be administered to any warm- or cold-blooded animals susceptible to infection with pathogenic microorganisms. Human and non-human animals may benefit as hosts.

Administration can be parenteral, but preferably oral or intranasal, depending upon the natural route of infection. In farm animals, for example, the vaccine may be administered orally by incorporation of the vaccine in feed or feed water. The dosage administered may be dependent upon the age, health and weight of the recipient, kind of concurrent treatment if any, and nature of the organism. Generally, a dosage of active ingredient will be from about $10^1$ to $10^{10}$ cells per application per host. The preferred dose for intranasal administration would generally be about $10^6$ organisms, suspended in 0.05 to 0.1 ml of an immunologically inert carrier. Peroral administration of a vaccine strain of, for example, *Salmonella typhi* developed according to the method described in this invention would probably require $10^6$ to $10^8$ organisms suspended in 1–2 mls of, for example, skim milk. The vaccines can be employed in dosage forms such as capsules, liquid solutions, suspensions, or elixirs, for oral administration, or sterile liquid for formulations such as solutions or suspensions for parenteral, intranasal or topical (e.g. wounds or burns) use. An inert, immunologically acceptable carrier is preferably used, such as saline, phosphate buffered saline or skim milk.

APPLICATION

Any microorganism capable of producing infectious disease can be genetically-attenuated according to the methods of the present invention to yield a useful and safe vaccine. Among these, bacteria, viruses and parasites are the most common microorganisms. The present invention is particularly concerned with bacterial mutations because of the ease of constructing the desired (recombinant) mutant strains. Table 1 lists common bacterial infections and the microorganisms which cause them. The list is not designed to be all inclusive but simply exemplary of the large number of bacteria which may be utilized. The hosts may be any human or non-human animal.

Having now generally described this invention, a more complete understanding can be obtained by reference to certain specific examples, which are included for purposes of illustration only and are not intended to be limiting unless otherwise specified.

TABLE 1

Some Common Bacterial Infections

| Disease | Bacterium |
|---|---|
| Meningitis | *Haemophilus influenzae* |

TABLE 1-continued

Some Common Bacterial Infections

| Disease | Bacterium |
| --- | --- |
|  | *Neisseria meningitidis* |
| Tuberculosis | *Mycobacterium tuberculosis* |
| Fowl cholera | *Pasteurella multocida* |
| Pertussis | *Bordetella pertussis* |
| Plague | *Pasteurella pestis* |
| Anthrax | *Bacillus anthracis* |
| Septicemia, pneumonia, | *Pseudomonas aeruginosa* |
| Typhoid fever | *Salmonella typhi* |
| Pneumonia | *Streptococcus pneumoniae,* |
|  | *Mycoplasma pneumoniae,* |
|  | *Staphylococcus aureus* |
| Coliform enteritis | *Escherichia coli* |
| Dental caries | *Streptococcus mutans* |
| Cholera | *Vibrio cholerae* |
| Gonorrhea | *Neisseris gonorrheae* |

PREPARATION OF A VACCINE AGAINST H. INFLUENZAE INFECTION

Background

*Haemophilus influenzae* type b is the major cause of endemic meningitis in children (Haggerty and Ziai, Adv. Ped. 13:129, 1964; Wehrle et al., Pediatrics 44:991, 1968; and Smith and Haynes, Pediatrics 50:723, 1972) and a significant cause of fatal epiglottitis, obstructive bronchiolitis, otitis media, septic arthritis, laryngitis, cellulitis and pneumonia in both children and adults. *H. influenzae* also causes meningitis in adults. At least 10,000 cases of meningitis due to *H. influenzae* type b occur annually in the United States. Rapid diagnosis and treatment with ampicillin or chloramphenicol usually leads to recovery. The mortality rate, however, has remained at 5-10%, and a significant number (30-50%) of those who do recover, suffer permanent neurological damage.

The recent emergence of a plasmid mediating drug resistance in *H. influenzae* type b has compromised antibiotic therapy in those areas where it has appeared (Center for Disease Control, Morbidity and Mortality Weekly Rep., 23:77, 1974). The precedent of the rapid dissemination of such plasmids worldwide indicates that within a short time antibiotics will no longer be effective in the control of *H. influenzae* infections. The specter of totally antibiotic-resistant *H. influenzae* type b together with the high incidence of serious permanent neurological sequelae make it imperative to develop new methods to control infections by this organism. Currently available purified polysaccharide vaccines for *H. influenzae* are not effective in very young children—those most likely to succumb to this organism. The need for an effective, safe vaccine against *H. influenzae* infection is therefore acute.

A recombinant strain of *H. influenzae* containing three ts mutations conveying the same phenotype was prepared using transformation as described in the present invention.

Materials and Methods

The following abbreviations are used throughout the following description of the preparation of a vaccine against *H. influenzae* infection.

A/b, antibiotic
BHI, brain heart infusion
cfu, colony forming unit
DMSO, dimethyl sulfoxide
DNA, deoxyribonucleic acid
$Em^{R,S}$, erythromycin-resistant, -sensitive
g, gram
$Km^{R,S}$, kanamycin-resistant, -sensitive
l, liter
mg, milligram
ml, milliliter
NAD, nicotinamide adenine dinucleotide
$Nal^{R,S}$, naladixic acid-resistant, -sensitive
$Nb^{R,S}$, novobiocin-resistant, -sensitive
NG, nitrosoguanidine, N-methyl-N'-nitro-N-nitrosoguanidine
PRP, polyribophosphate
$Rif^{R,S}$, rifamycin-resistant, -sensitive
RR, reversion rate
$Sm^{R,S}$, streptomycin-resistant, -sensitive
ts, temperature-sensitive
u, micron
ug, microgram
ul, microliter
$Vm^{R,S}$, viomycin-resistant, -sensitive

Bacteria

Two basic strains of *H. influenzae* were used in this work: the rough type d strain (strain 001) and a derivative resistant to the antibiotics, Em, Km, Nb, Sm, Vm and Nal (strain EKNSVNal). Strain 001 (ATCC #31517) and EKNSVNal both exhibit the characteristics described for *H. influenzae* in Bergey'Manual of Determinative Bacteriology, (7th edition, 1957) pp. 406-408—they are gram-negative rods, 0.2-0.3 by 0.5-2.0 microns, occurring singly and in pairs, occasionally in short chains. They require the growth factors nicotinamide adenine dinucleotide and hemin. EKNSVNal has been deposited at the ATCC and has the #31514.

Growth Media

*H. influenzae* was passaged routinely on brain heart infusion (BHI) (2.5% w/v) agar supplemented with hemin (20 ug/ml) and NAD (10 ug/ml) or chocolate agar. Liquid cultures were grown in supplemented BHI broth. Selective platings were on supplemented BHI agar containing the appropriate antibiotic.

Mutagenesis, Enrichment and Isolation

Figure 1:
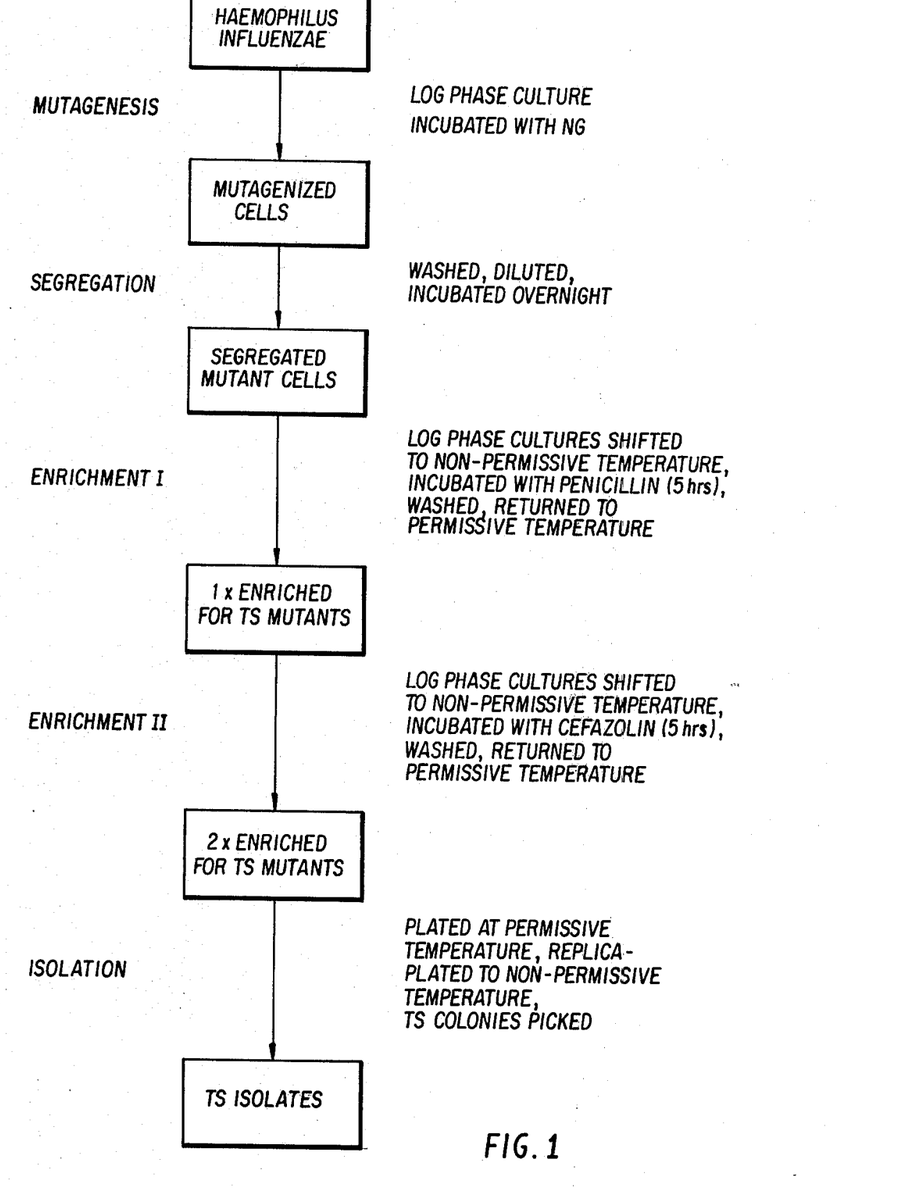

The protocol followed for isolating ts mutants of *H. influenzae* (001 and EKNSVNal) is outlined in FIG. 1. Since it may be necessary to colonize the upper respiratory tract with the vaccine strain, at least transiently, in order to alert the immune system, two types of ts mutant were sought. The classical "tight" mutant which ceases replication immediately after transfer to the nonpermissive temperature was routinely isolated by following the procedure described in FIG. 1. Mutants which "coast" for two or three generations after transfer to the restrictive temperature were isolated by delaying addition of antibiotic. Mutants with cut-off temperatures of 32°-36° C. were also sought by varying the temperatures at which the enrichments were performed.

Preliminary Characterization of Mutants

The ts mutants isolated by the procedures described above were tested to determine temperature cut-off points by streaking on chocolate agar plates and incubation at 27°, 30°, 32°, 34° and 36° C. Those mutants which grew along the primary streak but which were unable to form single colonies at the restrictive temperature were designated "coasters". Classical "tight" mutants were of course unable to grow at all above their temperature cut-off point.

The reversion rates of the individual mutant strains were determined by spreading $1-2 \times 10^9$ cells on chocolate agar plates which were incubated at the restrictive temperature. "Coasters" in liquid culture were always incubated at the restrictive temperature for 1 hour before plating.

The ability of "coasters" to continue growth after transfer to the non-permissive temperature was tested in liquid culture and "coasting" and final arrest monitored by absorbance at 600 nm and quantitation of colony-forming units.

Genetic Mapping

Figure 2:
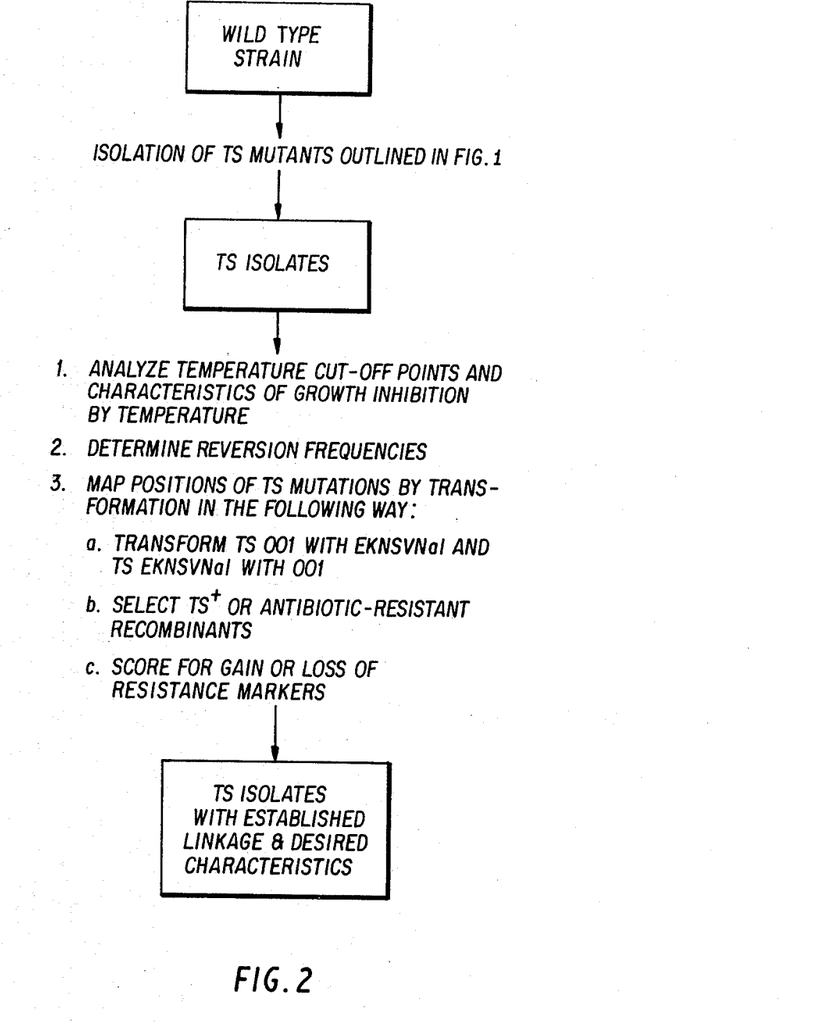
FIG. 2 describes the general strategy employed for locating and characterizing ts lesions in mutated strains of *H. influenzae*.
Figure 3:
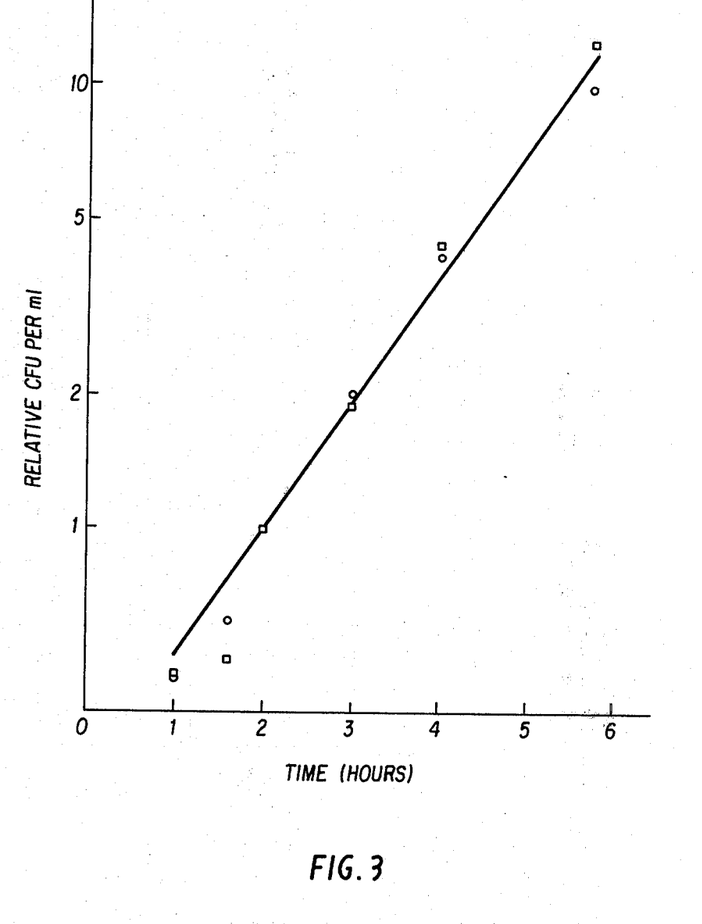
FIG. 3 describes the growth curves of the multiple-mutant strain, A214-A/3-C2/13 (o) and the wild-type, 001 (□), at 29° C.
Figure 4:
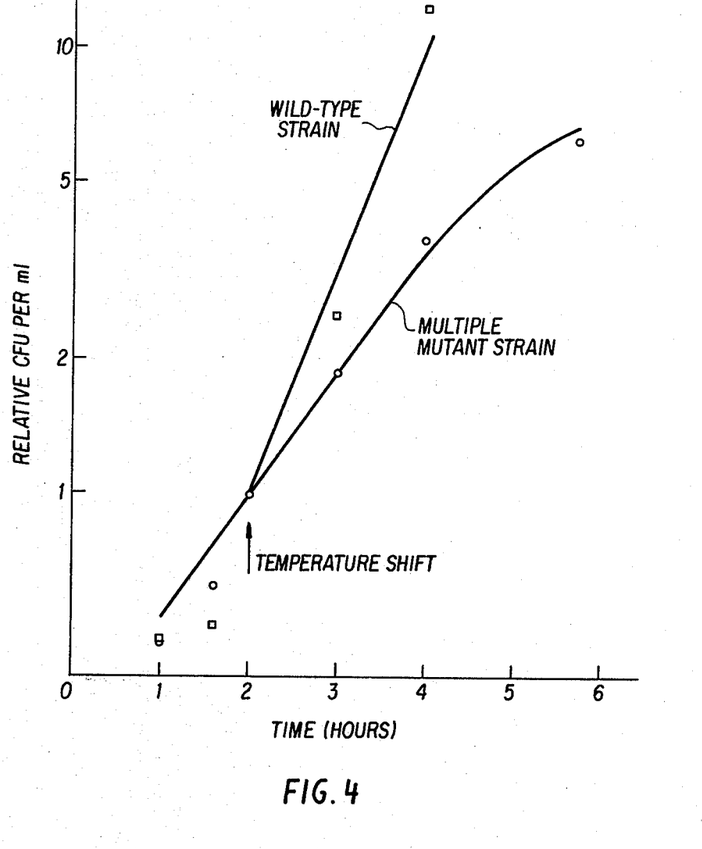
FIG. 4 describes the growth curves of the multiple-mutant strain, A214-A/3-C2/13 (o) and the wild-type, 001 (□), after temperature shift from 29° C. to 34° C.
Figure 5:
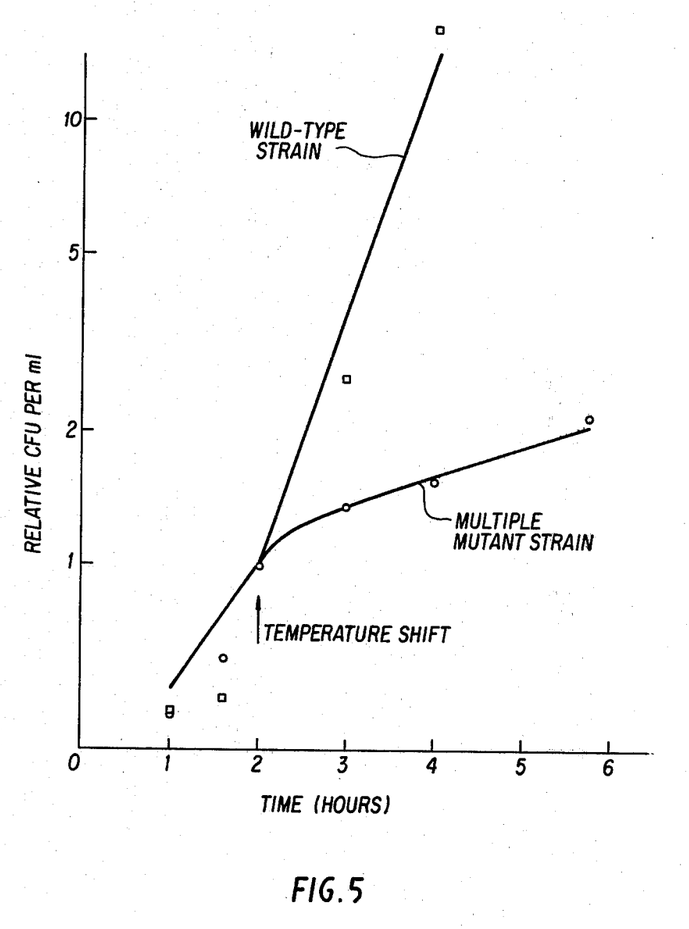
FIG. 5 describes the growth curves of the multiple-mutant strain, A214-A/3-C2/13 (o) and the wild-type, 001 (□), after temperature shift from 29° C. to 36° C.

Location of the ts lesions on the *H. influenzae* chromosome was accomplished by a series of transformations. The general strategy employed is outlined in FIG. 2. DNA from strain EKNSVNal was used to transform the ts 001 derivatives and transformants were selected on supplemented BHI agar containing the appropriate antibiotic. Antibiotic-resistant recombinants were then streaked on duplicate plates which were incubated at the permissive and non-permissive temperatures. If the ts lesion in an 001 mutant was "cured" by the acquisition of a gene conferring, for example Sm resistance, then that lesion was presumed to be linked to the Sm resistance gene.

The inverse experiment was also always performed—EKNSVNal DNA was used to transform ts 001 strains and the ts+ phenotype selected. The ts+ recombinants were then scored for the acquisition of antibiotic-resistance genes by replica-plating on supplemented BHI agar containing the appropriate antibiotics.

Similarly, ts EKNSVNal mutants were transformed with 001 DNA and restoration of the ts+ phenotype in the recombinants monitored for the concomitant loss of antibiotic-resistance. DNA from ts EKNSVNal strains was used to transform 001, antibiotic-resistance selected for at 27° C. and recombinants screened for temperature-sensitivity.

Transformation

The plate technique developed by Juni (Appl. Microbiol. 27:16, 1974) and modified by Clark et al., (Abstracts, A.S.M. Annual Meeting, 1977) was used for all transformations after preliminary experiments determined that the method was efficient at temperatures as low as 27° C. DNA was prepared by lysing cells ($1-2 \times 10^9$/ml) suspended in supplemented BHI broth containing 0.02% SDS and the preparation sterilized by heating at 60° C. for 15 minutes. Overnight plate cultures of the recipient bacteria were smeared on fresh chocolate agar and thoroughly mixed with one drop of DNA delivered from a 0.1 ml pipette. The plates were incubated for 3 hours (when ts+ recombinants were sought) or 7-18 hours (when antibiotic-resistant transformants were desired) at 30° C. and transformants streaked on chocolate agar or supplemented BHI agar containing the appropriate antibiotic. Those plates were then incubated at 36° C. in the former case and at 27° C. in the latter.

Purification of Mutant Alleles

Although NG is an excellent mutagen its tendency to induce additional mutations, both closely linked and distant from the gene of interest (Adelberg et al., Biochem. Biophys. Res. Comm. 18:788, 1965 and Hirota et al., J. Mol. Biol. 35:175, 1968), can cause problems. It is therefore desirable that, once the selected mutation has been deemed suitable it be transferred from the mutagenized "dirty" strain to a "clean" background. Accordingly, when the ts lesions had been mapped and linkage established to antibiotic-resistance markers, the genes were transformed into 001. DNA from the ts mutants generated in EKNSVNal was used to transform 001 and the transformants plated on supplemented BHI agar containing the appropriate antibiotic. Antibiotic-resistant recombinants were then screened for the presence of the ts gene. The reversion rates of the ts mutation were confirmed. Those ts derivatives of 001 whose lesions had been located near an antibiotic-resistance gene were first rendered antibiotic-resistant by transforming the appropriate marker from the "clean" EKNSVNal into the strain and monitoring for retention of temperature-sensitivity. The $A/b^R$-ts linked gene was then transformed into the "clean" 001 strain. In this way both sides of the antibiotic-resistance linked ts genes were purged of "contaminating" mutations induced by nitrosoguanidine treatment.

Final Strain Construction.

The 001 strains carrying the "clean" ts genes were combined by transformation, using the appropriate antibiotics for selection. Double recombinants were tested first for a reduction in reversion rate. The presence of the second ts gene was confirmed by recovering it in a second transformation to a ts+ strain. Triple recombinants could only be tested by recovery of the three ts genes in separate transformations.

Results

Single Mutant Isolates

Following the scheme outlined in FIG. 1 three strains which contained "coaster" ts mutations linked to selectable markers and which exhibited appropriate reversion frequencies and cut-off temperatures were selected. Their properties are listed in Table 2.

TABLE 2

MUTANT DERIVATIVES OF STRAINS 001 AND EKNSVNal

| Number | Temp. cut-off | Linkage | Reversion Rate |
|---|---|---|---|
| A/3 | 34° C. | $Km^R$ | $6 \times 10^{-8}$ |
| A214 | 34° C. | $Sm^R$ | $1 \times 10^{-8}$ |
| C2/13 | 34° C. | $Em^R$ | $1 \times 10^{-7}$ |

Recombinant Strain

The three ts lesions were combined in a single strain by sequential transformations. A214 was first transformed with A/3 DNA, $Km^R$ recombinants were selected and analyzed for lowered reversion frequencies. The presence of the ts lesion linked to $KM^R$ was confirmed by using DNA from the recombinant to transform 001. Maintenance of the ts lesion linked to $Sm^R$ was confirmed in a similar way. DNA from strain C2/13 was used to transform the recombinant A214-A/3 strain to $Em^R$. The presence of all three ts lesions was confirmed by recovering them in separate transformations of 001 (as described above). The reversion rates of these strains are listed in Table 3.

Both the double and triple recombinant strains have been deposited with the American Type Culture Collection, strain #'s 31515 and 31516 respectively. The taxonomy of the strains is identical with the starting strains, with the following modifications: growth is optimal at 29° C., inhibited at 34° C. and limited to two divisions at 36° C; the strain is resistant to the antibiotics kanamycin, streptomycin and erythromycin.

TABLE 3

PARENTAL AND RECOMBINANT STRAINS

| Strain | Reversion Rate | |
|---|---|---|
| | Observed | Calculated |
| A214 | $1 \times 10^{-8}$ | — |
| A/3 | $6 \times 10^{-8}$ | — |
| C2/13 | $1 \times 10^{-7}$ | — |
| A214-A/3 | $<3 \times 10^{-9}$ | $6 \times 10^{-16}$ |
| A214-A/3-C2/13 | $<3 \times 10^{-9}$ | $6 \times 10^{-23}$ |

Encapsulation of the Master Strain

The recombinant strain constitutes a master strain which is suitable for use as a vaccine against untypable strains of *H. influenzae* and, by transformation with DNA encoding the genes responsible for capsule formation, can be modified to produce vaccine strains against any and all of the six serotypes of *H. influenzae*. This modification of the master strain can be accomplished by preparing DNA from an encapsulated strain, using the DNA in a transformation mixture as described above, and plating the recombinants on supplemented BHI agar containing antiserum to the appropriate capsular polysaccharide—the encapsulated recombinants can be identified by the presence of an antigen-antibody precipitin "halo" surrounding the colonies.

What is claimed as new and intended to be covered by Letters Patent is:

1. A biologically pure culture of an avirulent bacterial strain useful as a vaccine, wherein said avirulent strain is derived from a virulent bacterial strain by introducing into said virulent strain at least two mutations of the same phenotype which render said virulent strain avirulent, while permitting said avirulent strain to retain immunogenicity;

wherein said phenotype is a temperature-sensitive phenotype which suppresses growth at the normal body temperature of a host for said virulent strain.

2. The avirulent strain of any of claim 1 wherein said bacterium is *H. influenzae*.

3. The avirulent strain of claim 2 wherein said bacterium is *H. influenzae* A214-A/3.

4. The avirulent strain of claim 2 wherein said bacterium is *H. influenzae* A214-A/3-C2/13.

5. The strain of any of claim 1 wherein said avirulent strain contains at least three mutations of the same phenotype.

6. The strain of any of claim 1 wherein said phenotype is such that growth will occur for at most 7 cell divisions after contact with the normal body temperature of said host.

7. The strain of claim 6 wherein growth will occur for at most 3 cell divisions after contact with the normal body temperature of said host.

* * * * *

UNITED STATES PATENT AND TRADEMARK OFFICE
CERTIFICATE OF CORRECTION

PATENT NO. : 4,337,314
DATED : June 29, 1982
INVENTOR(S) : M.P. Oeschger et al

It is certified that error appears in the above—identified patent and that said Letters Patent is hereby corrected as shown below:

On the title page correct the "References Cited" as follows:

In the second patent cited (U.S. 3,856,935), please correct the spelling of the inventor's name to read --Germanier-- instead of "Geornanier".

Column 10, line 28, please delete "which" and substitute therefor --with--;

Column 10, line 45, please delete "the" and substitute therefor --and--.

Column 18, line 13, delete "any of".

Signed and Sealed this

Twenty-fifth Day of January 1983

[SEAL]

Attest:

GERALD J. MOSSINGHOFF

Attesting Officer    Commissioner of Patents and Trademarks